United States Patent [19]
Peterson et al.

[11] Patent Number: 5,733,868
[45] Date of Patent: Mar. 31, 1998

[54] POLY(AMINO ACID) ADHESIVE TISSUE GRAFTS

[75] Inventors: Dale R. Peterson, Carmel, Ind.; Samuel I. Stupp, Champagne, Ill.

[73] Assignee: DePuy Orthopaedics, Inc., Warsaw, Ind.

[21] Appl. No.: 633,118

[22] Filed: Apr. 16, 1996

[51] Int. Cl.$^6$ .......................... A61B 17/08; A61K 37/02; C09J 201/00
[52] U.S. Cl. .......................... 514/2; 156/328; 156/336; 524/20
[58] Field of Search .......................... 514/2; 156/328, 156/336; 524/20

[56] References Cited

U.S. PATENT DOCUMENTS

| | | | |
|---|---|---|---|
| 4,157,418 | 6/1979 | Heilmann | 424/355 |
| 4,172,934 | 10/1979 | Heilmann | 526/298 |
| 4,242,208 | 12/1980 | Wallace et al. | 424/177 |
| 4,438,198 | 3/1984 | Schmer | 435/178 |
| 4,440,750 | 4/1984 | Glowacki et al. | 424/95 |
| 4,595,713 | 6/1986 | St. John | 523/105 |
| 4,694,103 | 9/1987 | Krepski et al. | 562/450 |
| 4,902,508 | 2/1990 | Badylak et al. | 424/95 |
| 4,956,178 | 9/1990 | Badylak et al. | 424/551 |
| 5,171,579 | 12/1992 | Ron et al. | 424/486 |
| 5,197,973 | 3/1993 | Pang et al. | 606/214 |

OTHER PUBLICATIONS

Anderson, James M. et al., Poly-α-Amino Acids as Biomedical Polymers, Biocompatibility of Tissue Analogs, vol. 1, Chapter 4, pp. 67–88 (1985).

Ijiri, S. et al., Influence of Sterilization on Bone Morphogenetic Protein, Fourth World Biomaterials Congress, p.21, Apr. 24–28, 1992.

Ijiri, S. et al., Effect of Sterilization on Bone Morphogenetic Protein, Journal of Orthopaedic Research, vol. 12, pp. 628–636, 1994.

Kalb, Claudia et al., Hope for Damaged Joints, Newsweek, p. 55, Jan. 29, 1996.

Kenley, Richard A. et al., Biotechnology and Bone Graft Substitutes, Pharmaceutical Research, vol. 10, No. 10, pp. 1393–1401, 1993.

Kohn, Joachim et al., Polymerization Reactions Involving the Side Chains of β–L–Amino Acids, J. Am. Chem. Soc., 109 pp. 817–820, 1987.

Pinholt, Else Marie et al., Bone Induction by Composites of Bioresorable Carriers and Demineralized Bone in Rats: A Comparative Study of Fibrin–Collagen Paste, Fibrin Sealant, and Polyorthoester With Gentamicin, J. Oral Maxillofac. Surg., 50:1300–1304, 1992.

Pulapura S. et al., Biomaterials Based on "Pseudo"–Poly(Amino Acids): A Study of Tyrosine Derived Polyiminocarbonates, Polymer Preprints, vol. 31, No. 1, pp. 233–234, Apr. 1990.

Sigma Chemical Company Biochemicals Organic Compounds and Diagnostic Reagents, pp. 1963–1965, (1996).

Stupp, Samuel I. et al., Organoapatites: Materials for Artificial Bone I. Synthesis and Microstructure, Journal of Biomedical Materials Research, vol. 26, 169–183, 1992.

Stupp, Samuel I. et al., Organoapatites: Materials for Artificial Bone. II. Hardening Reactions and Properties, Journal of Biomedical Materials Research, vol. 27, 289–299, 1993.

Stupp, Samuel I. et al., Organoapatites: Materials for Artificial Bone. III. Biological Testing, Journal of Biomedical Materials Research, vol. 27, pp. 301–311, 1993.

*Primary Examiner*—Nathan M. Nutter
*Attorney, Agent, or Firm*—Barnes & Thornburg

[57] ABSTRACT

A composition and method for repairing damaged connective tissue is provided. The composition comprises pseudo-poly(amino acids) and/or classic poly(amino acids) that exhibit adhesiveness for connective tissues. The composition is formed into an adhesive tissue repair implant and pressed against the damaged tissue to adhere the adhesive composition to the tissue.

15 Claims, No Drawings

POLY(AMINO ACID) ADHESIVE TISSUE GRAFTS

FIELD OF THE INVENTION

The present invention relates to biodegradable polymeric adhesives and methods of repairing biological structures. More particularly, the present invention is directed to biodegradable polypeptides that adhere to and effect repair of biological structures such as cartilage within the body.

BACKGROUND AND SUMMARY OF THE INVENTION

Effecting rapid, suitable repair of large bone and connective tissue defects caused by wounds, surgery, etc. has been a longstanding goal in the orthopedic field. One approach to effecting this repair has been to implant various matter into bone defects. This matter ultimately disintegrates or becomes an integral part of the healed structure. For example, it is well known to introduce into the body bioresorbable materials, such as collagen, tricalcium phosphate, and plaster of paris to fill bone defects. See, for example, U.S. Pat. No. 4,347,234.

Tissue augmentation compositions have also been implanted into the body for connective tissue repair. See, for example, U.S. Pat. No. 4,595,713. These compositions include soft or moldable polymeric materials that are designed to occupy the space where tissue regeneration is needed. These polymeric materials eventually are replaced by the hard or soft regenerated tissue. Since connective tissue is often soft and wet, it can be difficult to attach the augmentation composition to the tissue.

Researchers have attempted to use "fibrin glue" for tissue adhesives, hemostasis, and delivery of bioactive compounds or cells. Fibrinogen concentrates when mixed with thrombin (usually from a xenogeneic source) form a cross-linked fibrin gel. Widespread use of fibrin glue has, however, been hampered by several factors. First, fibrinogen concentration and purity vary widely from patient to patient and even among lots of pooled donors. Storage stability of the fibrinogen is also variable. Importantly, fibrin glue is too weak an adhesive for many attractive applications. What is needed is a moldable pressure-sensitive adhesive composition that adheres to the bone or connective tissue, which effects repair of the damaged site, and that degrades in vivo into nontoxic residues that are naturally occurring metabolites.

It is therefore an object of the present invention to provide a pressure-sensitive adhesive composition that adheres to biological surfaces.

A further object of the present invention is to provide a pressure-sensitive adhesive composition that adheres to wet connective tissue within the body.

Still another object of the present invention is to provide a biodegradable polypeptide that exhibits adhesiveness and adheres to wet connective tissue within the body.

Yet another object of the present invention is to provide a method for repairing damaged connective tissue.

According to the present invention a pressure-sensitive adhesive composition is provided that comprises at least two different poly(amino acids). Each poly(amino acid) has the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula $aX+bY+cZ$ wherein a, b, and c represent the respective mole fractions of the amino acids X, Y, and Z; $a=0$ to 1, $b=0$ to 1, and $c<1$; and $a+b+c=1.0$. In addition, X is selected from glutamate, asparagine, aspartate, and glutamine. Y is selected from lysine and arginine. Z is an amino acid selected from cysteine, methionine, serine, threonine, glycine, alanine, valine, leucine, and isoleucine.

In an alternative embodiment, a pressure-sensitive adhesive composition is provided that comprises a divalent or multivalent monomer and a poly(amino acid) of the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula $aX+bY+cZ$ wherein a, b, and c represent the respective mole fractions of the amino acids X, Y, and Z; $a=0$ to 1, $b=0$ to 1, and $c<1$; and $a+b+c=1.0$. In addition, X is selected from glutamate, asparagine, aspartate, and glutamine. Y is selected from lysine and arginine. Z is an amino acid selected from cysteine, methionine, serine, threonine, glycine, alanine, valine, leucine, and isoleucine. The monomer component of the pressure-sensitive adhesive composition is selected from glutamate, asparagine, aspartate, glutamine, lysine, arginine, and histidine.

A method for repairing damaged connective tissue is also provided in accordance with the present invention. The method comprises the steps of selecting a pressure-sensitive adhesive composition that comprises two or more different poly(amino acids). Each poly(amino acid) has the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula $aX+bY+cZ$; $a=0$ to 1, $b=0$ to 1, and $c=1$; and $a+b+c=1.0$. In addition, X is selected from glutamate, asparagine, aspartate, and glutamine. Y is selected from lysine and arginine. Z is an amino acid selected from cysteine, methionine, serine, threonine, glycine, alanine, valine, leucine, and isoleucine. The pressure-sensitive adhesive composition is then formed into an adhesive tissue-repair implant and pressed against the connective tissue so that the tissue-repair implant adheres to the tissue.

In an alternative embodiment, a method is provided for repairing damaged connective tissue. The method comprises the steps of selecting a pressure-sensitive adhesive composition that comprises a divalent or multivalent monomer and a poly(amino acid) of the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula $aX+bY+cZ$ wherein a, b, and c represent the respective mole fractions of the amino acids X, Y, and Z; $a=0$ to 1, $b=0$ to 1, and $c<1$; and $a+b+c=1.0$. X is selected from glutamate, asparagine, aspartate, and glutamine. Y is selected from lysine and arginine. Z is an amino acid selected from cysteine, methionine, serine, threonine, glycine, alanine, valine, leucine, and isoleucine. The monomer is selected from glutamate, asparagine, aspartate, glutamine, lysine, arginine, and histidine. The pressure-sensitive adhesive composition is then formed into an adhesive tissue repair implant and pressed against the connective tissue so that the tissue repair implant adheres to the tissue.

In yet another embodiment, a method for repairing damaged connective tissue is provided. The method comprises the steps of selecting a pressure-sensitive adhesive composition that comprises a pseudo-poly(amino acid) or a poly(amino acid) of the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula $aX+bY+cZ$ wherein a, b, and c represent the respective mole fractions of the amino acids X, Y, and Z; $a=0$ to 1, $b=0$ to 1, and $c<1$; and $a+b+c=1.0$. In addition, X is selected from glutamate, asparagine, aspartate, and glutamine. But, when X is only aspartate, $b>0$. Y is selected from lysine and arginine, and Z is an amino acid selected from cysteine, methionine, serine, threonine, glycine, alanine, valine, leucine, and isoleucine.

Additional objects, features and advantages of the invention will become apparent to those skilled in the art upon consideration of the following detailed description and preferred embodiments exemplifying the best mode of carrying out the invention as presently perceived.

DETAILED DESCRIPTION OF THE INVENTION

It has been discovered that certain poly(amino acids) exhibit adhesive properties toward soft connective tissues such as cartilage and hard connective tissues such as bone. These poly(amino acids) may be used to form a pressure-sensitive adhesive composition (hereinafter "PSA") that is capable of adhering to and effecting repair of such connective tissue. Poly(amino acids) that exhibit adhesive properties have a weight average molecular weight of about 500 to about 500,000, preferably about 10,000 to about 80,000, and most preferably, about 15,000 to about 50,000. The term poly(amino acid) as used in the specification and claims comprises: (1) classical poly(amino acids) of the formula $H_2N\text{—}Q\text{—}COOR_2$ in which Q is the divalent residue of a polypeptide and $R_2$ is H, a metal cation, or ammonium, and (2) pseudo-poly(amino acids), as will be described in greater detail later in the specification.

A PSA in accordance with the present invention exhibits an adhesiveness on connective tissue. In one embodiment, the PSA comprises two or more different poly(amino acids), each of the formula $H_2N\text{—}Q\text{—}COOR_2$ wherein Q is a divalent residue of a polypeptide formed from 1 to 3 species of amino acids; The amino acid components of Q are represented by the formula $aX+bY+cZ$, wherein a, b, and C represent the respective mole fractions of the amino acids X, Y, and Z; $a=0$ to 1, $b=0$ to 1, and $c<1$; and $a+b+c=1.0$.

Alternatively, the PSA comprises a divalent or multivalent monomer and a poly(amino acid) of the formula $H_2N\text{—}Q\text{—}COOR_2$ in which Q is a divalent residue of a polypeptide formed from 1 to 3 species of amino acids. The amino acid components of Q are represented by the formula $aX+bY+cZ$ in which a, b, and c represent the respective mole fractions of the amino acids X, Y, and Z; $a=0$ to 1, $b=0$ to 1, and $c<1$; and $a+b+c=1.0$.

In each of the embodiments of the present invention X is selected from glutamate, asparagine, aspartate, and glutamine. Y is selected from lysine and arginine. Z is selected from cysteine, methionine, serine, threonine, glycine, alanine, valine, leucine, or isoleucine. Amino acids, however, need not be selected from Y when particular divalent or multivalent monomers (as will be discussed hereafter) are present in the composition. A wide variety of polypeptides in a wide variety of ratios may be used in accordance with the present invention. The polypeptides suitable for use with the present invention are commercially available from Sigma Chemical Company, Inc., St. Louis, Mo.

In particular, it is understood that the amino acids may be arranged so that in any particular polypeptide a may equal 0 if b is greater than 0; b may equal 0 if a is greater than 0; c may equal 0; a may be greater than b; a may be greater than c; b may be greater than a; b may be greater than c; c may be greater than a; c may be greater than b; a may equal c; b may equal c; or a may equal b so long as c does not equal 1.

Particular divalent or multivalent monomers may be used in the present invention. Amino acids with two or more positive charges at physiological pH, such as lysine, arginine, or histidine, form complexes with poly(amino acids) bearing negative charges at physiological pH. Likewise, amino acids with two or more negative charges such as aspartate or glutamate are used to form complexes with poly(amino acids) bearing positive charges. However, it is understood that other biocompatible multivalent molecules may be used to form adhesive complexes in accordance with the present invention.

Select groups of amino acids are specifically excluded from use as homopolymers in the method of the present invention. For example, amino acids with aliphatic side chains have been found to exhibit unacceptably low interaction with the biological surface. However, it is understood that they could be considered as chain extenders or modulators along with cysteine, methionine, serine, and threonine in mixed polymers. Amino acids with aromatic side chains are specifically excluded from the present invention because they have been found to exhibit low rates of diffusion in the body. Moreover, although histidine has an amino side chain, this amino acid is omitted from the polypeptides of the present invention. Histidine has limited interaction with the biological surface, but may be used to complex with the polyamino acids as a monomer.

Pseudo-poly(amino acids) may be used in formulating the PSA of the present invention. Pseudo-poly(amino acids) differ from the poly(amino acids) described above in that dipeptide monomers are covalently bound through other than the normal peptide linkages. Pseudo-poly(amino acids) suitable for use in accordance with the present invention are those having the requisite adhesive character and prepared using the chemistry described, for example in Kohn, J. and Langer, R., Polymerization Reactions Involving the Side Chains of α-L-Amino Acids, J. Amer. Chem. Soc., 109, 917 (1987) and Pulapura, S. and Kohn, J., Biomaterials Based on "Pseudo"-Poly(Amino Acids): A Study of Tyrosine Derived Polyiminocarbonates, J., Polymer Preprints, 31, 23 (1990), each of which are incorporated herein by reference. The pseudo-poly(amino acids) can be used alone or in combination with the mixtures of classical poly(amino acids) and pseudo-poly(amino acids) in adhesive formulations in accordance with the invention.

A suitable poly(amino acid) exhibits adhesive properties on different substrates, one dry (glass) and the other water swollen poly(2-hydroxyethyl methacrylate) (hereinafter, "pHEMA") on glass to simulate wet tissues. The poly(amino acid) withstands a maximum stress (on a glass substrate) of about 1,000 Pa to about 150,000 Pa, more preferably about 10,000 Pa to about 40,000 Pa, and most preferably, about 12,000 Pa to about 16,000 Pa. The poly(amino acid) withstands a maximum stress (on a pHEMA substrate) of about 600 Pa to about 90,000 Pa, more preferably about 2500 Pa to about 40,000 Pa, and most preferably about 5500 to about 8500 Pa.

Moreover, the PSA is moldable by hand at a temperature of about 60° C. or below. Preferably, the PSA is moldable at about 4° C. to about 60° C., more preferably at about 15° C. to about 50° C., and most preferably at about 20° C. to about 30° C. The degree of moldability of the PSA at a selected temperature is dependent upon the characteristics of the poly(amino acid) selected as well its molecular weight. The PSA of the present invention remains moldable after it has been implanted within the body. Moreover, poly(amino acid) components of the PSA will degrade in vivo into nontoxic residues that are naturally occurring metabolites. The rate that the PSA degrades varies drastically depending upon the poly(amino acid)(s) selected and upon the implant location. The PSA completely degrades in vivo between about two hours to well over a year.

The PSA composition may be used as a graft for soft connective tissue repair or may be used to attach another material in place in the soft tissue site. The PSA may be formed mostly of poly(amino acids). However, a variety of other compounds may also be included in the PSA composition of the present invention to control the mechanical characteristics of the composition.

It is understood that the PSA in accordance with the present invention is suitable for repairing bone. When used as a bone graft composition, the PSA comprises from about 10 to about 100 percent by weight poly(amino acid), more preferably about 30 to about 70 percent by weight poly (amino acid), and most preferably about 50 to about 65 percent by weight poly(amino acid). When used as a bone graft composition the PSA comprises a filler.

The filler may be particulate, fibrous, organic, inorganic, or a mixture of both organic and inorganic. Suitable fillers comprise autogenous bone chips, tricalcium phosphate ("TCP"), hydroxylapatite ("HA"), powdered/dried small intestine submucosa as described in U.S. Pat. Nos.: 4,902, 508 and 4,956,178, bioglass granules, synthetic polymers, $CaCO_3$, $CaSO_4$, or collagen. Preferably, the filler is particulate and has an average particle size of about 50 μm to about 2000 μm, more preferably about 75 μm to about 700 μm, and most preferably, about 100 μm to about 500 μm. The PSA of the present invention preferably includes about 0 to about 90 weight percent, more preferably about 30 to about 70 weight percent, and most preferably about 35 to about 50 weight percent filler.

The PSA composition of the present invention may comprise optional ingredients such as bioactive agents. Suitable bioactive agents may, for example, be extracted from whole blood, packed red cells, platelets, plasma (fresh or fresh frozen plasma), serum, skin, bone, cartilage, tendon, microorganisms, synthetic proteins, etc. Suitable proteins can be any one of a wide variety of classes of proteins, such as keratins, collagens, albumins, globulins, hormones, enzymes, or the like. The material can be simple peptides, simple proteins, or conjugated proteins, such as glycoproteins, mucoproteins, lipoproteins, heme proteins, nucleoproteins, or the like. The significant factor is that the biological material has chemical and physical properties that are important to its physiological function.

Bioactive agents prefered for use in the present invention are growth factors, growth factor binding proteins, or cells. Examples of suitable growth factors include: a fibroblast growth factor, a transforming growth factor (e.g., TGF-$\beta_1$), a bone morphogenetic protein, epidermal growth factor, or a platelet-derived growth factor.

Examples of growth factor binding proteins are insulin-like growth factor binding proteins (IGFBP's) such as IGFBP's 3 and 5. Examples of suitable cells comprise bone marrow cells and mesenchymal stem cells. The bioactive agent can also be an osteogenic agent that stimulates or accelerates generation of bone upon implantation into a bone defect site. Examples of osteogenic agents comprise demineralized bone powder, morselized cancellous bone, aspirated bone marrow, bone or cartilage forming cells or their precursors, and other bone sources.

The biologically active agent may also be an antibacterial substance. Examples of useful antibacterial agents comprise gentamicin and vancomycin.

The PSA composition may further comprise extraneous proteins. These extraneous proteins include, for example, gelatin and bovine serum albumin. Moreover, antioxidants may be included in the PSA of the present invention. Antioxidants suitable for use include tocopherol, citric acid, butylated hydroxyamisole, butylated hydroxytoluene, tertiary butylhydroquinone, propyl gallate, ascorbate, and other antioxidants that are "generally recognized as safe" by the Food and Drug Administration.

Thus the PSA can be prepared by blending the poly(amino acids) with one or more bioactive agents and optionally other excipients, for example, additives to optimize retention of biological activity and polymer functionality during sterilization, and sterilizing and packaging the implant formulation for surgical use. Sterilization can be accomplished by radiation with about 1 to about 3 mRad of gamma radiation or electron beam radiation. If the biologically active agent is a biologically active protein or peptide, biological activity can be optimized during sterilization by including in the formulation an extraneous protein, for example albumin or gelatin, and a free radical scavenger (antioxidant), for example propyl gallate, 3-t-butyl-4-hydroxyanisole (BHA) or ascorbic acid, in an amount effective to retard radiation induced degradation of the biologically active peptide. The sterilization is preferably conducted at low temperature, for example –70° C. When a filler is used in the composition with a biologically active peptide or protein, it is advantageous to form a mixture of the biologically active compound and an extraneous protein such as albumin or gelatin, and coat the filler with that formulation prior to blending the filler into the poly(amino acids).

In employing the method of the present invention, a surgeon or other caregiver determines the size of the cavity/void to be filled or the dimensions of the repair site. The PSA is then selected from one of the above described poly(amino acids) of the formula $H_2N$—Q—$COOR_2$ in which Q is a divalent residue of a polypeptide formed from 1 to 3 species of amino acids and $R_2$ is H, a metal cation, or ammonium. The amino acid components of Q are represented by the formula aX+bY+cZ, wherein a, b, and c represent the respective mole fractions of the amino acids X, Y, and Z in addition a+b>0 and c<1 and a+b+c=1. The amino acids X, Y, and Z are selected as previously discussed.

After the PSA has been selected, it is removed from the packaging. The packaging is a barrier package that prevents water vapor from contacting the PSA. The packaging, however, may be any one of a wide variety of containers. The caregiver then forms the PSA into an adhesive tissue repair implant. This forming may be by hand, mechanically, or using any number of well-known techniques for shaping an implant. The PSA is formed by hand at approximately room temperature into the dimensions compatible with the repair site. Preferably, the PSA is formed to the exact dimensions of the cavity/void to be filled, and in the case of soft connective tissue repair, to the dimensions of the repair site. The PSA is then applied to the repair site in a manner that permits the adhesive composition to adhere to the biological material for a time sufficient to effect repair thereof. The caregiver presses the molded PSA composition against the damaged, and often wet tissue. Since the PSA composition has adhesive properties, it will stick to either bone or to cartilage for a time sufficient to repair of the connective tissue.

EXAMPLE 1

The adhesion characteristics of pressure-sensitive adhesive compositions were determined by tensile testing according to the following procedure:

Glass slides were cleaned by first immersing them in a hot sulfuric acid bath for 10 minutes. The slides were rinsed thoroughly with ultrapure water. Then they were placed in a warm ammonium hydroxide:hydrogen peroxide (4:1 by volume) bath for 1 minute. The glass slides were again rinsed with ultrapure water, and dried with filtered nitrogen. The clean glass slides are the dry glass substrates.

Aqueous solutions of 3% by weight poly(amino acid) were made using nano-pure water. This solution was placed on a face of the clean glass slide (4.84 $cm^2$ of exposed area) and dried under vacuum for 3 hours. All samples were stored in a desiccator at room temperature before mechanical testing.

Water swollen pHEMA was used as a second test substrate in order to simulate wet tissue. The films of pHEMA, were formed from 4% by weight solution of pHEMA in methanol, placed on a face of a cleaned glass slide 4.84 $cm^2$ of exposed area. The solution was dried with nitrogen gas followed by 3 hours vacuum.

Mechanical testing of the glass test substrates was done using the Series 4400 Instron. The adhesive properties of the poly(amino acid) films were tested on the glass substrate. The poly(amino acid) film slides were pressed on a clean dry glass slide with a force of 5 Newtons for 5 minutes. The Instron was then used to measure the stress and strain at which the two glass slides separated at an angle of about 90° relative to the face. The separation speed was 0.5 mm per minute. The results of the testing of the homopolymers are illustrated in Table 1.

A separate adhesion test was carried out on the water swollen pHEMA substrate in order to simulate a wet tissue surface. The above-described pHEMA film, cast on glass, was placed in a 100% humidity chamber for 30 minutes before testing. The poly(amino acid) slides were pressed on a water swollen pHEMA coated slide with a force of 5 Newtons for 5 minutes. The Instron was then used to measure the stress and strain at which the two slides separated at an angle of about 90° relative to the face. The separation speed was 0.5 mm per minute. The results of the testing of the homopolymers are illustrated in Table 1.

TABLE 1

HOMOPOLYMERS

| Polymer* (M.W.) | Glass | | Swollen pHEMA | |
|---|---|---|---|---|
| | max. stress (Pa) | max. strain | max. stress (Pa) | max. strain |
| pGlu (1000) | 6500 | 0.60 | 0 | 0 |
| pGlu (15300) | 3400 | 0.65 | 1000 | 0.20 |
| pLys (22700) | 2800 | 0.30 | 650 | 0.12 |
| pLys (42000) | 10000 | 0.70 | 2300 | 0.23 |
| pGln (3500) | 9000 | 0.85 | 0 | 0 |

*All poly(amino acids) were of L configuration

Surprisingly, various homopolymers, such as pGlu (15300), pLys (22700), and pLys (42000) were found to stick to the pHEMA substrate. It was found that all of the homopolymers adhere to the glass substrate.

It was determined that the adhesive strength of different materials may be manipulated by changing the homopolymer and/or the molecular weight of the homopolymer. The present invention is not limited to the above amino acids, but can be extrapolated to other amino acids of their class. In addition, the homopolymers could be substituted with mixed polymers such as copolymers, a terpolymer, block copolymers, or mixtures thereof as is described hereafter.

EXAMPLE 2

Glass and pHEMA substrates were prepared and poly (amino acid) adhesives were deposited as described in Example 1. Using the glass and pHEMA substrates, the effect of various weight ratios of different monomers on the adhesion characteristics of selected homopolymers, were determined. The results of the testing are illustrated in Table 2.

TABLE 2

POLYMER-MONOMER COMPLEXES

| Complex (MW) [wt. Ratio] | Glass | | Swollen pHEMA | |
|---|---|---|---|---|
| | max. stress (Pa) | max. strain | max. stress (Pa) | max. strain |
| pGlu (1000):Lys [2:1] | 1100 | 0.12 | 1000 | 0.07 |
| pGlu (1000):Lys [1:2] | 9000 | 0.60 | 0 | 0 |
| pGlu (15300):Lys [2:1] | 8000 | 0.60 | 2300 | 0.40 |
| pGlu (15300):Lys [1:1] | 10000 | 0.80 | 1500 | 0.16 |
| pLys (22700):Glu [1:1] | 0 | 0 | 0 | 0 |
| pLys (22700):Glu [1:2] | 0 | 0 | 0 | 0 |
| pLys (42000):Glu [1:0.8] | — | — | 5500 | 0.50 |
| pLys (42000):Glu [1:2] | 0 | 0 | 1150 | 0.25 |
| pGln (35000):Lys [1:0.6] | 3500 | 0.30 | 1250 | 0.13 |
| pGln:Lys [1:0.7] | 4800 | 0.65 | 0 | 0 |
| pGln:Lys [1:1] | 0 | 0 | 1200 | 0.20 |
| pGln:Glu [1:1] | 5000 | 0.45 | 0 | 0 |
| pGln:Glu [1:2] | 3000 | 0.30 | 0 | 0 |

It was found that the adhesion of pGlu (1000 and 5300) on the glass substrate improved as the amount of Lys monomer was added. On the water swollen pHEMA substrate, a higher pGlu to Lys monomer ratio favored adhesion. The adhesion of pLys (22700 and 42000) on the glass substrate decreased as the amount of Glu monomer increased. Finally, the addition of Glu monomer improved the adhesion of pLys (42000) to the water swollen pHEMA substrate.

These results are not limited to the above examples, but demonstrate how a specific adhesive strength to different types of material may be achieved. The PSA of the present invention can be tailored by the type of amino acid homopolymer used, or mole weight of the homopolymer, to produce a desired adhesive property to different connective tissues. The homopolymers could be substituted with mixed polymers such as copolymers, a terpolymer, block copolymers, or mixtures thereof.

EXAMPLE 3

Glass and pHEMA substrates were prepared and poly (amino acids) adhesives were deposited as described in Example 1. Using the glass and pHEMA substrates, the effect of various weight ratios and blends of homopolymers on the adhesion characteristics of selected polymer blends were determined. The results of the testing is illustrated in Table 3.

TABLE 3

POLYMER BLENDS

| Blend of pGln (3500) with amino acid homopolymer (MW) [wt. Ratio] pGln:homopolymer | Glass | | Swollen pHEMA | |
|---|---|---|---|---|
| | max. stress (Pa) | max. strain | max. stress (Pa) | max. strain |
| pGlu (1000) [1:0.4] | 3000 | 0.40 | 0 | 0 |
| pGlu (1000) [1:0.8] | 5000 | 0.55 | 3300 | 0.25 |
| pGlu (1000) [1:2] | 2800 | 0.55 | 0 | 0 |
| pGlu (15300) [1:0.9] | 7500 | 0.60 | 2300 | 0.30 |
| pGlu (15300) [1:2] | 16000 | 1.50 | 8500 | 1.00 |
| pLys (22700) [1:0.3] | 2000 | 0.20 | 0 | 0 |
| pLys (22700) [1:0.8] | 13000 | 0.95 | 0 | 0 |
| pLys (22700) [1:2] | 6000 | 0.42 | 0 | 0 |
| pLys (24000) [1:0.5] | 1800 | 0.25 | 0 | 0 |
| pLys (42000) [1:0.8] | 9000 | 0.85 | 5500 | 0.90 |
| pLys (42000) [1:0.84] | 11000 | 1.75 | — | — |
| pLys (42000) [1:0.9] | 8000 | 1.40 | — | — |
| pLys (42000) [1:1.2] | 10000 | 0.90 | — | — |
| pLys (42000) [1:1.25] | 13000 | 2.30 | 9000 | 1.10 |
| pLys (42000) [1:2] | 3100 | 0.18 | 3500 | 0.55 |

It was discovered that polymer blends of pGln with pGlu (15300) showed a noticeable improvement over pGln homopolymer (see Table 1) in adhesion and strength and strain on both the glass and pHEMA substrates. The sample pGln:pGlu (15300) [1:2] was one of the most preferred a were also among the most preferred adhesives. pGln and pLys (42000) by themselves exhibited good adhesion to the glass substrate but their blends were even better adhesives.

Blends of amino acid homopolymers produced the most preferred adhesives. This was a small sample of the large number of useful combinations of amino acid polymer blends suitable for use with the present invention. The blends may be expanded to three or more amino acid polymers and comprise monomers if needed to customize the adhesive characteristics to the target substrates. The homopolymers could be substituted with mixed amino acid polymers such as copolymers, a terpolymer, block copolymers, or mixtures thereof.

Although the invention has been described in detail with reference to certain preferred embodiments, variations and modifications exist within the scope and spirit of the invention as described and defined in the following claims.

What is claimed is:

1. A pressure-sensitive adhesive composition comprising two different poly(amino acids), each of the formula $H_2N—Q—COOR_2$ wherein Q is a divalent residue of a polypeptide formed from 1 to 3 species of amino acids, $R_2$ is H, a metal cation, or ammonium and wherein the amino acid components of Q are represented by the formula aX+bY+cZ wherein a, b, and c represent the respective mole fractions of the amino acids X, Y, and Z; a=0 to 1, b=0 to 1, and c<1; and a+b+c=1.0, and wherein X is selected from glutamate, asparagine, aspartate, and glutamine, Y is selected from lysine and arginine, and Z is an amino acid selected from cysteine, methionine, serine, threonine, glycine, alanine, valine, leucine, and isoleucine, and wherein the composition exhibits an adhesiveness of about 600 to about 150,000 Pa.

2. The composition of claim 1, wherein the composition is moldable at about 4° C. to about 60° C.

3. The composition of claim 1, further comprising a monomer selected from the group consisting of glutamate, aspartate, lysine, and histidine and arginine.

4. The composition of claim 1, wherein the polypeptide bears a negative charge at about physiological pH and further comprising an amino acid monomer with two or more positive charges.

5. The composition of claim 4, wherein the monomer is selected from the group consisting of lysine, arginine, or histidine.

6. The composition of claim 1, wherein the polypeptide bears a positive charge at about physiological pH and further comprising an amino acid monomer with two or more negative charges.

7. The composition of claim 6, wherein the monomer is selected from the group consisting of aspartate or glutamate.

8. The composition of claim 1, further comprising a bioactive agent.

9. A pressure-sensitive adhesive composition comprising (1) a poly(amino acid) of the formula $H_2N—Q—COOR_2$ wherein Q is a divalent residue of a polypeptide formed from 1 to 3 species of amino acids, $R_2$ is H, a metal cation, or ammonium and wherein the amino acid components of Q are represented by the formula aX+bY+cZ wherein a, b, and c represent the respective mole fractions of the amino acids X, Y, and Z; a=0 to 1, b=0 to 1, and c<1; and a+b+c=1.0;
  (a) wherein X is selected from glutamate, asparagine, aspartate, and glutamine;
  (b) Y is selected from lysine and arginine; and
  (c) Z is an amino acid selected from cysteine, methionine, serine, threonine, glycine, alanine, valine, leucine, and isoleucine;

(2) a monomer selected from the group consisting of glutamate, asparagine, aspartate, glutamine, lysine, arginine, and histidine; and (3) wherein the composition exhibits on adhesiveness of about 600 to about 150,000 Pa.

10. The composition of claim 9, wherein the polypeptide bears a positive charge at about physiological pH and the monomer is selected from the group consisting of aspartate and glutamate.

11. The composition of claim 9, wherein the polypeptide bears a negative charge at about physiological pH and the monomer is selected from the group consisting of lysine, arginine, and histidine.

12. A method for repairing damaged connective tissue, the method comprising the steps of (1) selecting a pressure-sensitive adhesive composition comprising a pseudo-poly(amino acid), or a poly (amino acid) of the formula $H_2N—Q—COOR_2$ wherein Q is a divalent residue of a polypeptide formed from 1 to 3 species of amino acids, $R_2$ is H, a metal cation, or ammonium and wherein the amino acid components of Q are represented by the formula aX+bY+cZ, wherein a, b, and c represent the respective mole fractions by the amino acids X, Y, and Z, a+b is >0, and a+b+c=1.0;
  (a) wherein X is selected from glutamate, asparagine, aspartate, or glutamine;
  (b) wherein if X is only aspartate, b>0;
  (c) wherein Y is selected from lysine or arginine; and
  (d) wherein Z is selected from cysteine, methionine, serine, threonine, glycine, alanine, valine, leucine, isoleucine;

(2) forming an adhesive tissue repair implant from the selected pressure-sensitive adhesive composition; and (3) pressing the tissue repair implant against the damaged tissue to adhere the adhesive composition to the tissue.

13. A method for effecting repair of damaged connective tissue, the method comprising the steps of
   (1) selecting a pressure-sensitive adhesive composition comprising
      (a) a poly(amino acid) of the formula $H_2N$—Q—$COOR_2$ wherein Q is a divalent residue of a polypeptide formed from 1 to 3 species of amino acids, $R_2$ is H, a metal cation, or ammonium and wherein the amino acid components of Q are represented by the formula $aX+bY+cZ$ wherein a, b, and c represent the respective mole fractions of the amino acids X, Y, and Z; a=0 to 1, b=0 to 1; c<1; and a+b+c=1.0;
         (i) wherein X is selected from glutamate, asparagine, aspartate, and glutamine;
         (ii) Y is selected from lysine and arginine; and
         (iii) Z is an amino acid selected from cysteine, methionine, serine, threonine, glycine, alanine, valine, leucine, and isoleucine; and
      (b) a monomer selected from the group consisting of glutamate, aspartate, lysine, histidine, and arginine;
   (2) forming an adhesive tissue repair implant from the selected pressure-sensitive adhesive composition; and
   (3) pressing the tissue repair implant against the damaged tissue to adhere the adhesive composition to the tissue.

14. A method for effecting repair of damaged connective tissue, the method comprising the steps of
   (1) selecting a pressure-sensitive adhesive composition comprising two different poly(amino acids), each of the formula $H_2N$—Q—$COOR_2$ wherein Q is a divalent residue of a polypeptide formed from 1 to 3 species of amino acids, $R_2$ is H, a metal cation, or ammonium and wherein the amino acid components of Q are represented by the formula $aX+bY+cZ$ wherein a, b, and c represent the respective mole fractions of the amino acids X, Y, and Z; a=0 to 1, b=0 to 1, and c<1; and a+b+c=1.0;
      (a) wherein X is selected from glutamate, asparagine, aspartate, and glutamine;
      (b) Y is selected from lysine and arginine; and
      (c) Z is an amino acid selected from cysteine, methionine, serine, threonine, glycine, alanine, valine, leucine, and isoleucine;
   (2) forming an adhesive tissue repair implant from the selected pressure-sensitive adhesive composition; and
   (3) pressing the tissue repair implant against the damaged tissue to adhere the adhesive composition to the tissue.

15. The method of claim 14, wherein the forming step comprises the step of maintaining the temperature of the adhesive composition at about 4° C. to about 60° C.

* * * * *